(12) United States Patent
James et al.

(10) Patent No.: US 8,202,550 B2
(45) Date of Patent: Jun. 19, 2012

(54) COMPOSITIONS FOR INTRANASAL ADMINISTRATION

(75) Inventors: Michael James, Ramsey (GB); Peter Josling, Catsfield (GB)

(73) Assignee: Nasaleze PPM Limited, Ramsey (GB)

( * ) Notice: Subject to any disclaimer, the term of this patent is extended or adjusted under 35 U.S.C. 154(b) by 771 days.

(21) Appl. No.: 11/665,148

(22) PCT Filed: Oct. 10, 2005

(86) PCT No.: PCT/GB2005/050179
§ 371 (c)(1),
(2), (4) Date: Feb. 18, 2010

(87) PCT Pub. No.: WO2006/040596
PCT Pub. Date: Apr. 20, 2006

(65) Prior Publication Data
US 2010/0297269 A1    Nov. 25, 2010

(30) Foreign Application Priority Data

| Oct. 11, 2004 | (GB) | ................................. 0422582.7 |
| Feb. 10, 2005 | (GB) | ................................. 0502792.5 |
| Jul. 19, 2005 | (JP) | ................................. 2005-209097 |
| Sep. 21, 2005 | (GB) | ................................. 0519213.3 |

(51) Int. Cl.
| A61K 36/00 | (2006.01) |
| A61K 36/53 | (2006.01) |
| A61K 36/84 | (2006.01) |
| A61K 36/16 | (2006.01) |
| A61K 36/8962 | (2006.01) |
| A61K 36/481 | (2006.01) |
| A61K 31/733 | (2006.01) |
| A61K 36/31 | (2006.01) |
| A61K 36/254 | (2006.01) |
| A61K 36/752 | (2006.01) |
| A61K 36/61 | (2006.01) |
| A61K 35/534 | (2006.01) |

(52) U.S. Cl. ........ 424/725; 424/728; 424/736; 424/737; 424/742; 424/745; 424/747; 424/752; 424/754; 424/764

(58) Field of Classification Search .................. None
See application file for complete search history.

(56) References Cited

U.S. PATENT DOCUMENTS

2005/0142072 A1*   6/2005   Birch et al. ................ 424/46

FOREIGN PATENT DOCUMENTS

| EP | 0606486 A1 | 6/1993 |
| EP | 0943326 A1 | 2/1997 |
| EP | 1093818 A1 | 7/1999 |
| GB | 2378176 A | 3/2001 |
| WO | WO92/16196 | 3/1992 |

* cited by examiner

*Primary Examiner* — Qiuwen Mi
(74) *Attorney, Agent, or Firm* — Head, Johnson & Kachigian, P.C.

(57) ABSTRACT

Pharmaceutical compositions are for administration to the nasal tract. In particular, dry powder compositions are cellulose, and in particular hydroxypropylmethylcellulose (HPMC), and one or more therapeutic agents. It has been shown that administration of HPMC to the nasal cavity is capable of enhancing natural mucus. These powders, and the gel that forms when they are administered to the nasal tract, have now surprisingly been found to be a very effective way of intranasally administering therapeutic agents, and in particular, herbal or homeopathic agents.

12 Claims, No Drawings

COMPOSITIONS FOR INTRANASAL ADMINISTRATION

The present invention relates to pharmaceutical compositions for administration to the nasal tract. In particular, the invention relates to dry powder compositions comprising cellulose, and in particular hydroxypropylmethylcellulose (HPMC), and one or more therapeutic agents. It has been shown that certain grades of HPMC are capable of enhancing natural mucus when administered to the nasal cavity. These powders, and the gel that forms when they are administered to the nasal tract, have now surprisingly been found to be a very effective way of intranasally administering therapeutic agents, and in particular, herbal or homeopathic agents.

Intranasal administration of pharmaceutical compounds is a known method of drug delivery. Dry powder formulations comprising therapeutic agents have been applied directly to the nasal membranes to achieve a rapid, local or systemic therapeutic effect on the epithelial cells lining the nose. Systemic delivery via the nasal mucosa has a number of beneficial properties. For example, the absorption of the pharmaceutically active agent into the bloodstream via the nasal mucosa can be rapid, and faster than, for example, absorption via the gastrointestinal tract following oral administration of an active agent. Nasal administration also allows "first pass" metabolism to be avoided, a problem associated with the oral administration of some pharmaceutically active agents. Further to this, it is also possible to use nasal administration for providing slower, sustained release of drugs.

However, intranasal drug administration has limitations. Firstly, the absorption of the therapeutic agent from the nasal passages, and therefore the local and/or systemic administration of the agent, can be limited as a result of factors such as the physicochemical characteristics of the therapeutic agent, the concentration and volume of the formulation administered, the site and pattern of deposition, and loss from the nasal cavity after administration. Intranasal drug administration can also be limited by factors related to nasal physiology, such as environmental conditions, enzymatic degradation and nasal blood flow.

Further to this, administration of compositions to the nose can adversely affect nasal tract physiology.

The airway epithelium is normally protected from dehydration and inhaled infectious and toxic agents by the presence of mucus. Mucus also has a very important role in preventing inhaled particles from reaching the delicate alveoli of the lungs.

Airway mucus is a complex mixture of proteins, enzymes, lipids and a sol phase composed of water and electrolytes. Some 95% of mucus is water and this water is bound in a viscoelastic gel containing mucins, which are large glycoproteins. Particles, such as dust, pollen and other allergens, and infectious agents, such as bacteria and viruses, are entrained in air which is inhaled into the nasal tract. The outer nose can filter out some of the larger airborne particles. Inside the nose, the shape of the nasal tract itself causes a "smoke ring" effect to occur so that smaller particles and bacteria present in the air stream within the nose are instantly separated out from the clean air and are concentrated at the periphery of the inhaled air stream. This allows the clean air to be inhaled into the lungs whilst the particles and infectious agents alight on the mucus which lines the nasal tract. As a result of the low surface tension of the mucus, the particles and infectious agents are immediately adsorbed and positively rendered harmless when they are trapped by the mucus.

People who suffer from allergic rhinitis and asthma, as well as other conditions associated with inhaled allergens, often have a reduced amount of mucus or mucus with abnormal properties. This appears to lead to their increased exposure to the allergens which are considered to be at least partially responsible for these conditions.

Nasal mucus is constantly being removed from the nasal tract by gravity, as well as by mucociliary clearance, whereby the beating of cilia located on the mucous membranes of the nasal tract moves the mucus to the throat for elimination via the digestive system. The removal of mucus from the nasal tract by mucociliary clearance is an important element of the defense of the ciliated nasal epithelium against inhaled allergens and infectious agents. Patients suffering from allergic rhinitis frequently have abnormally slow or prolonged mucociliary clearance, and this may well contribute to their condition.

Intranasal administration of known compositions can cause drying of the nasal mucosa and damage to the delicate nasal membrane and the cilia. This can adversely affect mucociliary clearance, and therefore damage the well-being of the nasal tract. Components regularly included in intranasal compositions can cause irritation, which is undesirable, although it is often transient. Compositions for intranasal administration also frequently include agents, such as adhesion agents, for the purpose of increasing the time for which the administered composition is resident within the nasal passage. Such agents will adhere to the mucous membranes and cilia in the nose. In doing so, the agents can cause discomfort and can adversely affect breathing. The adhesion of agents also, again, adversely affects mucociliary clearance and in doing so, interferes with the normal functioning of the nose.

However, the use of powdered cellulose as a vehicle for the therapeutic agent in intranasal compositions has been shown to have surprising benefits. Gels formed by administration of HPMC to the nasal cavity are capable of releasing or absorbing moisture, thereby allowing them to control the humidity in the nasal tract. If the humidity in the nasal tract increases, the gel absorbs moisture. If the humidity drops, the gel releases moisture. This means that the gel is able to provide a constant humidity in the nose. The humidity within the nasal tract in turn affects and controls the moisture content, and therefore the viscoelastic properties, of the natural mucus.

HPMC powders are generally classified in terms of their viscosity, measured as the viscosity of the HPMC in a 2% aqueous solution at 20° C. A therapeutically beneficial level of humidity is provided by compositions comprising HPMC with a viscosity of approximately 10 to 20 Pa·s (Pascal second), preferably approximately 13-17 Pa·s, more preferably approximately 14-16 Pa·s and most preferably approximately 15 Pa·s, the viscosity of the HPMC being measured as the viscosity of a 2% aqueous solution at 20° C., preferably using a Ubbelohde viscometer.

The viscoelasticity of mucus is important for its interaction with the cilia responsible for mucociliary clearance. Mucus with inadequate viscosity will be runny, and is likely to either drip out of the nose through the nostrils or run down the throat. Such runny mucus will also be less able to effectively act as a filter and trap airborne particles and infectious agents. Also, the beating cilia will be unable to move mucus which does not have adequate viscosity. Similarly, if the mucus is too viscous, the beating cilia will, again, be unable to move it, and the mucus will tend to clog the nasal tract, which can make breathing difficult, whilst also being extremely uncomfortable. Such thick mucus may also be less efficient in absorbing and trapping particles and infectious agents.

Correct mucal viscoelasticity is, therefore, essential for mucociliary clearance. Compositions comprising grades of HPMC that are capable of controlling the humidity in the nasal tract, and the gel that forms when they are administered to the nasal tract, are thus useful in the treatment and/or prevention of certain allergic conditions, such as allergic rhinitis, asthma and atopic eczema, of infections caused by inhaled infectious agents, such as bacteria and viruses, and of medical conditions associated with poor or abnormal natural mucus production.

Further to this, the use of these grades of powdered cellulose in compositions for intra-nasal administration avoids the disadvantages associated with other intranasally applied compositions, such as the drying out of the nasal mucosa and the associated discomfort and irritation.

In fact, it has also been found that mucociliary clearance can be normalised (that is, can be adjusted to a normal rate) by administering compositions comprising HMPCs which are capable of controlling the humidity in the nasal tract.

Patients suffering from allergic rhinitis often have longer mucociliary clearance times. Tests carried out in vivo using a non-invasive dye method have shown that the average time required for mucociliary clearance in subjects suffering from allergic rhinitis was reduced from 39 minutes to 18.15 minutes following 6 weeks of once-daily intranasal administration of a grade of hydroxypropylmethylcellulose having a viscosity of approximately 15 Pa·s. Thus, the intranasal administration of the HPMC normalised the rate of mucociliary clearance.

One might expect that this effect of the HPMC on mucociliary clearance would result in the compositions being effective for only a short period of time, as one would expect the HPMC gel to be quickly cleared from the nasal tract (usually in the to region of 18 minutes). However, this is not the case and subjects suffering from allergic rhinitis have surprisingly reported that they only need to administer the HPMC once or twice a day to enjoy the beneficial effects.

The inventors have now discovered that the benefits of intranasal administration of powdered HPMC can be utilized to provide an unexpectedly effective vehicle for the administration of one of more therapeutic agents. This is surprising, due to the way in which the powder compositions act when administered to the nasal cavity.

The therapeutic agent will become trapped within the gel that is formed when the powder compositions are administered to the nasal tract. Thus, one would expect the co-administered therapeutic agent to have little, if any, therapeutic effect.

However, it has been found that a therapeutic agent included in a composition according to the present invention produces a therapeutic effect, which may actually be more beneficial than the effect observed when the agent is not administered with powdered HPMC. The gel formed when the HPMC is administered to the nasal tract slowly releases moisture and any therapeutic agent which was co-administered. This results in a lasting therapeutic effect, with beneficial effects of the therapeutic agent reported for up to 24 hours following administration. In comparison, administration of active agents to the nasal tract in conventional intranasal compositions (such as liquid compositions or powder composition comprising little or no cellulose) typically provides therapeutic effects of relatively short duration.

Thus, according to a first aspect of the present invention, a dry powder intranasal composition is provided comprising hydroxypropylmethylcellulose with a viscosity of approximately 10-20 Pa·s (Pascal second), and one or more therapeutic agents.

In preferable embodiments, the viscosity of the HPMC is approximately 13-17 Pa·s, more preferably approximately 14-16 Pa·s, and most preferably approximately 15 Pa·s.

The use of HPMC as a vehicle for therapeutic agents for administration to the nose achieves controlled release of the therapeutic agent and promotes the correct functioning of mucociliary clearance and the well-being of the nose, whilst avoiding the need for, and the irritation and discomfort associated with the use of, additional agents, such as adhesive agents.

Compositions according to the present invention provide benefits over conventional intranasal compositions. Known intranasal compositions typically provide a rapid and transient rise in systemic blood levels of the therapeutic agent. In comparison, the sustained release of the active agent by compositions according to the present invention provides a consistent, lower blood concentration which is beneficial for certain active agents and may allow administration of smaller doses of the agent whilst still achieving the same or an improved therapeutic effect. The administration of smaller doses can reduce or completely avoid adverse side effects, which are frequently related to the size of the dose of active agent administered.

The sustained release of active agents in the nasal tract from the compositions according to the present invention is beneficial for certain active agents and it may allow one to administer smaller doses of the agent whilst still achieving the same or an improved therapeutic effect. This can reduce or completely avoid adverse side effects, which are frequently related to the size of the dose of active agent that is administered.

In certain embodiments, the therapeutic agent may have a local effect in the nasal tract. In alternative embodiments, the therapeutic agent may be absorbed into the bloodstream to provide a systemic effect. Alternatively, the therapeutic agent may provide both a local and systemic effect.

The term "therapeutic agent" as used herein denotes any active substance suitable for nasal administration to a patient (particularly a mammalian patient) in any composition, formulation or product in accordance with the present invention.

Compositions according to the present invention provide sustained release of a therapeutic agent or agents when administered intranasally. Preferably, the therapeutic agent is released over a period of 30 minutes, 1 hour, 2 hours, 4, 6, 8, 10 or 12 hours. Preferably, the compositions provide a therapeutic affect over a period of 30 minutes, 1 hour, 2 hours, 4, 6, 8, 10 or 12 hours from intranasal administration.

In particularly preferred embodiments, the therapeutic agent is a herbal or homeopathic agent rather than a pharmaceutical product.

The terms "homeopathic" and "herbal" as used herein refer to products derived from natural plant or mineral sources.

The term "pharmaceutical products" as used herein refers to an agent available only under prescription or that requires efficacy, toxicity and marketing approval from the Medicines and Healthcare Products Regulatory Agency before use.

Many people emphatically prefer not to take pharmaceutical products if at all possible, instead preferring to use herbal and/or homeopathic preparations, for both therapeutic and/or prophylactic purposes.

The herbal and homeopathic preparation market constitutes a huge industry, which grossed £4.5 billion in the UK alone last year. Yet the vast majority of herbal/homeopathic remedies are provided in oral or transdermal form. Such methods of administration, however, suffer from disadvantages. Tablets, for example, can be difficult for certain patients to swallow and can have a delayed onset of action. Also, many of the active agents within remedies for oral administration are metabolised before they are absorbed via the gastrointestinal tract. Delivery of drugs across the skin can be limited as a result of the stratum corneum, which forms an effective barrier membrane that limits the type of molecules that can be absorbed by the skin, and also the rate of absorption. In contrast, intranasal administration, as discussed above, can provide an effective means of administration.

It is also well known that the nasal mucosa are very sensitive to irritation, and toxicological considerations are a major limitation in the choice of therapeutic agent for nasal administration. Herbal or homeopathic remedies frequently exhibit no or minimal toxicity at the concentrations required to produce a therapeutic effect using the delivery system according to the present invention.

Therapeutic agents to be included in the compositions of the present invention include those understood by the skilled person to be homeopathic or herbal remedies. The therapeutic agent may be a homeopathic or herbal remedy which has one or more of the following properties: antibacterial and/or antifungal, antiviral, antibiotic, anti-inflammatory, anti-insomnia, cognitive enhancing, or properties that affect cardiovascular function (e.g. cardiotonic properties, antidysrythmic or anti-anginal properties, vasoconstriction or vasodilation properties or anti-hypertensive properties).

Specific therapeutic agent may include: aspirin, St John's Wort, valerian extract (which may include sesquiterpenes, valeric acid, iridoids, valepotriates, alkaloids, furanofuran lignans, amino acids, γ-aminobutyric acid, tyrosine, arginine, glutamine or any combination thereof), ginkgo biloba extract (which may include flavonoids, ginkgolides and bilobalides or any combination thereof), vitamins A, E or C, garlic, lime, one or more pro-biotics, ginger, ellagic acid, echinacea, Swedish flower pollen, black walnut hulls, lemongrass, wormwood, grapefruit seed extract, broccoli, digestive enzymes, hyaluronic acid, astralgus, rosehips, gentian, hypericum, horse chestnut, ginseng, green tea, phosphatidyl serine, phosphatidyl choline, citrus, pycnogenol, caffeine, quercitin, co-enzyme Q10, yarrow, tea tree, noni juice (*Morinda citrifolia*), lipase, fructo-oligosaccharide, inulin, black cumin (*Nigella sativa*) or allicin.

Compositions according to the present invention may comprise more than one therapeutic agent, provided that the combined agents are compatible with one another under conditions of storage and use.

Compositions according to the present invention may further comprise kali bichromium; a thickening agent such as a gum or starch; a disintegrant, such as sodium starch glycolate or cross-linked povidone; a release agent such as magnesium stearate; an emulsifying agent; a surfactant; pharmaceutically acceptable excipients; anti-caking agents; granulating agents; preservatives; such colorants as may be desired or any combination thereof.

In preferred embodiments of the present invention, the powder compositions do not include components which are often used in intranasal compositions (dry powders or solutions) which can cause irritation or affect ciliary movement, for example, solvents, such as propylene glycol, absorption enhancers, such as cyclodextrins or glycosides, or mucoadhesives such as chitosan. The use of such additives can be undesirable, as they can cause discomfort and interfere with the normal functioning of the nose, which can adversely affect breathing.

Compositions according to the present invention may further comprise a flavouring or signalling agent or additive such as menthol, mint, spearmint, peppermint, eucalyptus, lavender, citrus, lemon, lime, or any combination thereof.

The inclusion of such flavouring or signalling agents in the composition can provide the patient with pleasant sensory feedback upon use, which allows the patient to recognize that administration has occurred, and may aid the patient's recollection of administration. Such factors can improve patient compliance and provide a positive psychological effect.

It has also been found that including a flavouring agent enhances the prophylactic or therapeutic effect of powder compositions of the present invention. More specifically, compositions including mint, menthol and the like are thought to be more effective at treating allergic rhinitis and asthma than compositions of the invention which do not include a signalling agent.

The flavouring or signalling agents may also have a beneficial psychological effect on the subject. For example, formulations according to the present invention which include mint seem to have the effect of opening the airways and allowing easier breathing. This may be particularly beneficial when the formulations are used to treat patients suffering from asthma. Some patients, particularly those of a nervous disposition, tend to breathe in an irregular pattern. The administration of HPMC formulations including agents such as mint can provide a feel-good factor which can be effective in restoring normal breathing patterns.

In certain embodiment of the present invention, the combination of the HPMC, signalling agent and therapeutic agent is provided for sequential or simultaneous administration. The HPMC, signalling agent and therapeutic agent may be included together in a single preparation. Alternatively, the HPMC, signalling agent and therapeutic agent may be provided in separate preparations, for sequential administration. Where administration is sequential, the HPMC and/or signalling agent may be administered before or after the therapeutic agent, or both. Similarly, the therapeutic agent may be administered before or after the HPMC and/or signalling agent, or both.

Where the powdered HPMC and/or signalling agent are included in the same preparation as the therapeutic agent, this preparation is preferably in the form of a powder. Where the powdered HPMC and/or signalling agent are included in a separate preparation to the therapeutic agent, the HPMC is preferably in the form of a powder. The therapeutic agent may, however, be in any form and is preferably in a form suitable for nasal administration, such as in the form of a powder, liquid or cream or gel.

In a preferred embodiment of the present invention, the powdered HPMC comprises at least 50%, and preferably at least 60, 70, 80, 90, 95, 97 or 99% by total weight of the composition In a preferred embodiment of the present invention, the ratio of therapeutic agent to powdered HPMC in the composition (by weight) is between 0.1:9.9 and 1.9:8.1, 0.2:9.8 and 1.8:8.2, 0.5:9.5 and 1.5:8.5, 0.6:9.4 and 1.4:8.6, 0.8:9.2 and 1.2:8.8, 1.0:9.0 and 1.5:8.5, 1.5:8.5 and 2.0:8.0, 2.0:8.0 and 2.5:7.5, 2.5:7.5 and 3.0:7.0, 3.0:7.0 and 3.6:6.4, 3.6:6.4 and 4:6.0 or 2.5:7.5 and 3.6:6.4. More preferably, the ratio is between 2.5:7.5 and 3.6:6.4. Most preferably, the ratio is 3.3:6.7.

In a preferred embodiment of the present invention, the signalling agent comprises up to 50%, and preferably up to 40, 30, 20, 10, 5, 2, 1, 0.5 or 0.25% by total weight of the composition.

In another embodiment of the present invention, the combination of the HPMC and the therapeutic agent is provided for sequential or simultaneous administration. The HPMC and the therapeutic agent may be included together in a single preparation. Alternatively, the HPMC and the therapeutic agent may be provided in separate preparations, for sequential administration. Where administration is sequential, the HPMC may be administered before and/or after the pharmaceutically active agent. Alternatively, the active agent may be administered before and/or after the HPMC.

Where the HPMC and the therapeutic agent are included in separate preparations, the therapeutic agent may be in any form suitable for intranasal administration, including a powder, liquid or cream or gel.

According to an aspect of the present invention, a kit is provided, comprising a HPMC powder composition, and a therapeutic agent, for simultaneous or sequential administration.

According to another aspect of the present invention a kit is provided comprising a HPMC powder composition, a signalling agent and a therapeutic agent for simultaneous or sequential administration.

Powder ingredients may be blended together using a ribbon blender, or similar type of blender for approximately 15 to 20 minutes. The time of mixing is dependent upon the moisture content and compatibility of the powders. Ingredients preferably have a moisture content of less than 5%, as checked with the United States Pharmacopeia and National Formulary (USP/NF) loss on drying method.

A device which is suitable for dispensing the compositions according to the present invention are disclosed in British Patent Publication No. 2378176A. The bottles disclosed therein use a very simple mechanism for restricting the amount of powder which is dispensed. Whilst the amount of powdered cellulose delivered to the nasal tract in order to enhance natural mucus does not have to be precisely controlled, the administration of too much powder could potentially cause an uncomfortable blockage of the nasal tract and may even result in difficulty in breathing through the nose.

The compositions according to the present invention are preferably administered in amounts of between about 1 mg and about 10 mg per nostril. Preferably, the dose is between about 2.5 mg to about 7.5 mg, between 3 mg and about 7 mg, between about 4 mg and about 6 mg, or about 5 mg.

The present invention will now be further illustrated by the following Examples, which do not limit the invention in any way.

EXAMPLE 1

| Composition Ingredients: | % |
| --- | --- |
| Hydroxypropylmethylcellulose | 66.6 |
| Allicin | 33.3 |

Method of Preparation

All materials were checked with the relevant Certificate of Analysis. Ingredients were individually weighed out. The ingredients were then mixed using a ribbon blender, or similar type of blender for 20 minutes. The blended powder was then dispensed into an airtight container prior to use.

EXAMPLE 2

| Composition Ingredients: | % |
| --- | --- |
| Hydroxypropylmethylcellulose | 75 |
| Echinacea | 24.5 |
| Menthol | 0.5 |

Method of Preparation

All materials were checked with the relevant Certificate of Analysis. Ingredients were individually weighed out. The ingredients were then mixed using a ribbon blender, or similar type of blender for 20 minutes. The blended powder was then dispensed into an airtight container prior to use.

EXAMPLE 3

| Composition Ingredients: | % |
| --- | --- |
| Hydroxypropylmethylcellulose | 84 |
| Ginseng | 15 |
| Lavender | 1 |

Method of Preparation

All materials were checked with the relevant Certificate of Analysis. Ingredients were individually weighed out. The ingredients were then mixed using a ribbon blender, or similar type of blender for 20 minutes. The blended powder was then dispensed into an airtight container prior to use.

The invention claimed is:

1. A dry powder intranasal composition comprising:
   hydroxypropylmethylcellulose powder with a viscosity of approximately 10-20 Pas:
   one or more therapeutic agents; and
   a signaling agent, which together form a dry powder characterized in that the signaling agent allows a user to sense administration of the composition in the nasal cavity and is mint, spearmint, peppermint, eucalyptus, lavender, citrus, lemon, lime or any combination thereof and wherein the dry powder composition transforms to a gel upon contact with a nasal cavity.

2. A dry powder composition as claimed in claim 1, wherein the viscosity of the hydroxypropylmethylcellulose is approximately 15 Pas.

3. A dry powder composition as claimed in claim 1, wherein the therapeutic agent has a systemic effect upon intranasal administration.

4. A dry powder composition as claimed in claim 1, wherein the composition provides a sustained release of the therapeutic agent.

5. A dry powder composition as claimed in claim 1, wherein the therapeutic agent is a herbal or homeopathic agent.

6. A dry powder composition as claimed in claim 5, wherein the therapeutic agent has one or more of the following properties: antibacterial and/or antifungal, antiviral, antibiotic, anti-inflammatory, anti-insomnia, cognitive enhancing, or properties that affect cardiovascular function.

7. A dry powder composition as claimed in claim 5, wherein the therapeutic agent is: aspirin, St John's Wort, valerian extract, ginkgo biloba extract, vitamins A, E or C, garlic, lime, one or more pro-biotics, ginger, ellagic acid, echinacea, Swedish flower pollen, black walnut hulls, lemongrass, wormwood, grapefruit seed extract, broccoli, digestive enzymes, hyaluronic acid, astragalus, rosehips, gentian, hypericum, horse chestnut, ginseng, green tea, phosphatidyl serine, phosphatidyl choline, citrus, pycnogenol, caffeine, quercitin, co-enzyme Q10, yarrow, tea tree, noni juice, lipase, fructo-oligosaccharide, inulin, black cumin, allicin, or any combination thereof.

8. A dry powder composition as claimed in claim 1, wherein the powdered hydroxypropylmethylcellulose comprises at least 99% of the total weight of the composition.

9. A dry powder composition as claimed in claim 1, wherein the ratio of therapeutically active agent to powdered cellulose is between 2.5:7.5 and 3.6:6.4.

10. A composition as claimed in claim 1, wherein the signalling agent comprises up to 0.25% of the total weight of the composition.

11. A composition as claimed in claim 1, which is substantially free of irritants or other additives.

12. A device comprising a dry powder composition as claimed in claim 1, the device being suitable for delivering the composition to the nasal tract.

\* \* \* \* \*